United States Patent
Ledoux et al.

(10) Patent No.: US 10,190,863 B2
(45) Date of Patent: Jan. 29, 2019

(54) METHOD FOR MEASURING THE THICKNESS OF A LAYER OF RUBBER-LIKE MATERIAL

(71) Applicants: COMPAGNIE GENERALE DES ESTABLISSEMENTS MICHELIN, Clermont-Ferrand (FR); MICHELIN RECHERCHE ET TECHNIQUE S.A., Granges-Paccot (CH)

(72) Inventors: Thomas Ledoux, Clermont-Ferrand (FR); Denis Martin, Clermont-Ferrand (FR); Alexandre Pernot, Clermont-Ferrand (FR); Guillaume Heredia, Clermont-Ferrand (FR); Patrick Meneroud, Meylan (FR); Cédric Goeau, Meylan (FR)

(73) Assignee: Compagnie Generale des Etablissements Michelin, Clermont-Ferrand (FR)

( * ) Notice: Subject to any disclaimer, the term of this patent is extended or adjusted under 35 U.S.C. 154(b) by 37 days.

(21) Appl. No.: 15/535,138

(22) PCT Filed: Dec. 11, 2015

(86) PCT No.: PCT/EP2015/079454
§ 371 (c)(1),
(2) Date: Jun. 12, 2017

(87) PCT Pub. No.: WO2016/096661
PCT Pub. Date: Jun. 23, 2016

(65) Prior Publication Data
US 2017/0322012 A1  Nov. 9, 2017

(30) Foreign Application Priority Data
Dec. 17, 2014  (FR) .................................... 14 62589

(51) Int. Cl.
*G01M 17/02* (2006.01)
*G01B 7/06* (2006.01)
(Continued)

(52) U.S. Cl.
CPC ............... *G01B 7/10* (2013.01); *G01M 17/02* (2013.01); *G01N 27/72* (2013.01); *G01R 33/123* (2013.01)

(58) Field of Classification Search
CPC ... G01B 7/06; G01B 7/10; G01B 7/22; G01B 7/26; G01B 15/02; G01M 17/02; G01N 27/72; G01R 33/123
(Continued)

(56) References Cited

U.S. PATENT DOCUMENTS 3,675,375 A    7/1972  Enabnit et al. ............. 51/281 R
4,150,567 A *  4/1979  Prevorsek ............. G01M 17/02
                                                      73/146
(Continued)

FOREIGN PATENT DOCUMENTS

DE    35 07 651 C1    4/1986
DE    90 13 605 U1    1/1991
(Continued)

OTHER PUBLICATIONS

International Search Report issued by WIPO dated Mar. 22, 2016, in connection with International Application No. PCT/EP2015/079454 (with English translation attached).

*Primary Examiner* — Jermele M Hollington
*Assistant Examiner* — Steven Yeninas
(74) *Attorney, Agent, or Firm* — Venable LLP

(57) ABSTRACT

A method is provided for measuring a thickness of a layer of rubber-like material. The layer of rubber-like material includes a free face in contact with air and a face joined to an adjacent reinforcement made of elements electrically
(Continued)

insulated from one another. Each of the elements includes at least one hysteretic material having a magnetic permeability greater than the magnetic permeability of air. According to the method, a sensitive element, which emits an alternating magnetic field, is brought towards the layer of rubber-like material whose thickness is to be measured, hysteretic losses in the adjacent reinforcement are measured at terminals of the sensitive element, and a thickness of the layer of rubber-like material is evaluated based on the hysteretic losses.

10 Claims, 2 Drawing Sheets

(51) Int. Cl.
*G01N 27/72* (2006.01)
*G01R 33/12* (2006.01)

(58) Field of Classification Search
USPC ...... 324/207.17, 229, 230, 231, 644; 73/146
See application file for complete search history.

(56) References Cited

U.S. PATENT DOCUMENTS

| | | | |
|---|---|---|---|
| 4,297,878 A * | 11/1981 | Prevorsek | G01M 17/02 73/146 |
| 6,501,287 B1 * | 12/2002 | Baldwin | G01B 5/0014 324/670 |
| 7,578,180 B2 | 8/2009 | Lionetti et al. | 73/146 |
| 2009/0000370 A1 * | 1/2009 | Lionetti | G01B 7/26 73/146 |
| 2013/0057271 A1 * | 3/2013 | Garshelis | G01R 33/123 324/251 |
| 2014/0125330 A1 * | 5/2014 | Stanton | G01B 7/06 324/229 |
| 2016/0153763 A1 | 6/2016 | Ledoux et al. | G01B 7/26 |
| 2016/0161243 A1 | 6/2016 | Ledoux et al. | G01B 7/26 |
| 2016/0169657 A1 | 6/2016 | Ledoux et al. | G01B 7/26 |
| 2017/0038278 A1 | 2/2017 | Ledoux et al. | G01M 17/02 |

FOREIGN PATENT DOCUMENTS

| | | |
|---|---|---|
| EP | 0 100 009 A1 | 2/1984 |
| EP | 2 009 389 A1 | 12/2008 |
| EP | 2 706 351 A2 | 3/2014 |
| WO | WO 2008/059283 A1 | 5/2008 |

* cited by examiner

METHOD FOR MEASURING THE THICKNESS OF A LAYER OF RUBBER-LIKE MATERIAL

TECHNICAL FIELD

The invention lies within the field of tyres for vehicles, and more precisely within the field of the evaluation of the wear of such tyres.

RELATED ART

In a known way, the tread of a pneumatic tyre, or more simply a tyre, regardless of whether it is to be fitted on a passenger vehicle, a heavy transport vehicle, a civil engineering vehicle, or other vehicle, is provided with a tread pattern comprising, notably, pattern elements or elementary blocks delimited by various main, longitudinal, transverse or oblique grooves, the elementary blocks also possibly comprising various finer slits or sipes. The grooves form channels intended to discharge the water during running on wet ground, and define the leading edges of the tread pattern elements.

The initial depth of the tread is at its greatest when a tyre is new. This initial depth may vary according to the type of tyre in question, as well as the use for which it is intended; by way of example, "winter" tyres generally have a tread pattern depth greater than that of "summer" tyres. When the tyre becomes worn, the depth of the elementary blocks of the tread pattern decreases and the stiffness of these elementary blocks increases. The increase in the stiffness of the elementary tread pattern blocks causes a reduction in some performance characteristics of the tyre, such as the grip on wet ground. The water discharge capacity also decreases markedly when the depth of the channels of the tread pattern decreases.

It is therefore desirable to be able to monitor the development of the wear of the tread of a tyre. This monitoring is usually carried out by visual observation of the tread by the user or a mechanic, with or without actual measurement with a depth gauge. However, this observation is not very easy to carry out, notably on rear tyres which are harder to access, and furthermore it is not very precise.

Numerous proposals have been made to automate the measurement of the depth of tyre tread patterns. Such devices can be placed on the roadway on which vehicles run.

Thus there are known measuring devices based on optical systems, comprising cameras or lasers for example. However, these systems are relatively costly, and have proved to be impractical in use, since they have to be embedded in the roadway and require regular maintenance. Moreover, the reliability of their measurement is arguable, since the measurements may be subject to considerable interference due to soiling and the presence or spraying of water, mud, snow, etc.

There are also known systems, notably those proposed in U.S. Pat. No. 7,578,180 B2 and WO 2008/059283, for measuring the thickness of the tread of a tyre, comprising sensors sensitive to the eddy currents generated by an exciting magnetic field in the crown reinforcement of the tyre. These systems are placed on a roadway.

However, it has been found that these methods supply false or inaccurate measurements for some types of tyre. The present invention is therefore intended to overcome this drawback by providing a novel method for measuring the thickness of the tread.

BRIEF DESCRIPTION OF THE INVENTION

The invention relates to a method for measuring the thickness of a layer of rubber-like material, this layer of material comprising a free face in contact with the air and a face joined to an adjacent reinforcement made of elements electrically insulated from one another, each of these elements containing at least one hysteresis material having a magnetic permeability greater than the magnetic permeability of air. The elements electrically insulated from one another are preferably wires.

This method comprises the following steps:
   A step in which a sensitive element emitting an alternating magnetic field is brought towards the layer of material whose thickness is to be measured,
   A step in which hysteresis losses in the adjacent reinforcement are measured, these losses being measured at the terminals of the sensitive element, and
   A step in which the thickness of the layer of material is evaluated on the basis of these hysteresis losses.

The conditions for the application of a method according to the invention will be detailed with the aid of FIG. 3, which shows the magnetic characteristics of two different materials. Preferably, the hysteresis elements are all located at the same distance from the face of the layer joined to the reinforcement.

Also preferably, the size of the hysteresis elements is such that they prevent the appearance of eddy currents in the reinforcement.

The curve 210, in solid lines, is characteristic of the assembly of materials forming a tyre reinforcement. Starting with a magnetic excitation H of zero, when said magnetic excitation increases, the magnetic field B in the core of the tyre reinforcement also increases. In a second stage, when the magnetic excitation H decreases, the magnetic field B also decreases, but does not naturally return to a zero value when the excitation H is zero.

This phenomenon, characteristic of ferromagnetic materials, is known as hysteresis, and signifies that the magnetic state of the material depends on the preceding states. Alternatively, the curve 210 is said to be a hysteresis cycle found in conditions of periodic excitation, meaning that the excitation H is produced, for example, by a coil supplied with a sinusoidal signal.

When an element sensitive to magnetic excitation is brought towards a tyre, the ferromagnetic material present in the tyre reinforcement goes through this hysteresis cycle at the frequency of the supply signal the sensitive element. When this is done, said material undergoes heating which is known as hysteresis loss. These losses increase with the frequency of the supply signal of the sensor, and with the amplitude of the magnetic excitation to which the assembly forming the tyre reinforcement is subjected. Furthermore, they also depend on the surface inside the hysteresis cycle 210.

Thus, if the amplitude of the supply signal of the sensor is stable, the magnetic excitation to which the tyre reinforcement is subjected may vary, provided that the distance between the sensitive element and said reinforcement is varied. Any losses generated in the reinforcement depend directly on the distance between the sensitive element and the reinforcement.

The reinforcement of the tyre is embedded in a layer of rubber under the pattern elements which become worn during the life of a tyre. Thus, if the sensitive element is placed on the outer surface of the tyre, the distance between the sensitive element and the reinforcement will correspond to the quantity of material remaining. The level of wear of the tyre may therefore be evaluated by measuring the hysteresis losses generated in a tyre reinforcement.

The curve 211, in broken lines, shows the magnetic characteristic of a tyre reinforcement which would be result from the use of a non-ferromagnetic metal material, in the form of a thin aluminium sheet for example. In this case, there is no hysteresis cycle, since the material is non-magnetic. Consequently there are no hysteresis losses, and the method according to the invention cannot be used.

However, eddy current losses may be observed in this case, these losses appearing when the material satisfies two conditions:

on the one hand, the material is a good electrical conductor, which is the case in metallic materials, and, on the other hand, the material has a geometric shape having sufficient dimensions in at least two orthogonal directions.

Thus, in a configuration in which the tyre reinforcement comprises a metal sheet, for example an aluminium sheet, embedded in a layer of rubber, the material satisfies the two conditions defined above, since aluminium is a good electrical conductor and the sheet has at least a length and a width of more than a centimeter. In this case, eddy currents are indeed created.

However, in a configuration in which the tyre reinforcement consists of a set of metal reinforcing elements, notably cords, embedded in a layer of rubber, the elements being positioned parallel to one another, no eddy currents will be established in the reinforcement. This is because a reinforcement of this type has a magnetic characteristic 210 as shown in FIG. 3, and the assembly of rubber and ferromagnetic cords formed in this way is a hysteresis composite in terms of magnetism. In this case, the ferromagnetic cords are electrically conductive but have only one large dimension, in the direction of the length of the cord, because the other two dimensions, orthogonal to the direction of the length of the cord, are too small, being, for example, no greater than one percent of the main dimension of the cord in the direction of its length. Thus, the aforesaid conditions for the appearance of eddy currents are not fulfilled, and therefore no eddy currents are established in the reinforcement.

Furthermore, eddy currents cannot be established between one cord and another, since the cords are interconnected by a highly resistive rubber joint which prevents the flow of current.

Therefore, a method according to the invention is advantageously used in the case of a tyre reinforcement which contains at least one type of ferromagnetic hysteresis material in the form of cords, and which is such that the resistance measured between two points on this assembly shows that the overall resistivity of the composite formed in this way is at least one megohm meter, and more than ten megohm meter in some embodiments.

In the remainder of the description, the concepts of conductivity and resistivity will be used by turns to define a metal reinforcement of this type. It should be noted here that resistivity is the inverse of conductivity.

To find this value of resistivity, the resistance must be measured between two points located on two separate elements, or between two points located on the same non-metallic element. The expression "separate elements" is taken to mean, for example, a metallic reinforcing element and a body of rubber, or two separate metal reinforcing elements belonging to the same reinforcement.

In this exemplary embodiment, no eddy currents are established in the tyre reinforcement, and the sensitive element used in a method according to the present invention is not an eddy current sensor.

In a preferred embodiment, the step of bringing a sensitive element towards the layer of material consists in applying to the free face of the layer of material a housing in which the sensitive element is installed. Advantageously, the housing comprises, in addition to the sensitive element, an electronic measuring device.

In a preferred embodiment, the sensitive element is a solenoid, in one of the forms included in the group comprising a printed circuit and a copper wire wound with or without a ferromagnetic support.

In a preferred embodiment, the method further comprises the following steps:

The sensitive element is supplied with an alternating electrical signal, and

The frequency of this supply signal is made to vary.

Preferably, the supply signal of the sensitive element is selected with a frequency below a cut-off frequency of the sensitive element.

In a preferred embodiment, the method comprises the preliminary step of determining an appropriate excitation frequency of the coil.

In a preferred embodiment, the sensitive element is formed from turns, and the method is such that the step of bringing the sensitive element towards the layer of material consists in positioning the sensitive element in such a way that the plane parallel to the turns forming the coil is parallel to the surface of the free face.

BRIEF DESCRIPTION OF THE DRAWINGS

Other objects and advantages of the invention will be clearly apparent from the following description of some preferred, but non-limiting, embodiments, illustrated by the following drawings, in which.

DESCRIPTION OF THE BEST EMBODIMENT OF THE INVENTION

Figure 1A:
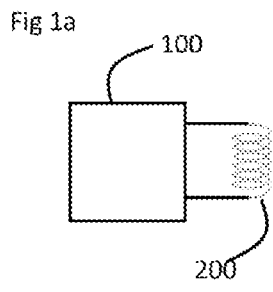
FIGS. 1a and 1b detail a first example of a sensitive element used in a method according to the invention, and curves representative of the frequency response of a sensitive element of this type.

FIG. 1a shows a first example of a sensitive element used in a method according to the invention. In this example, the sensitive element is a coil 200, connected to an electronic measurement circuit 100. Advantageously, these two elements are installed in a housing, not shown in the drawing, designed to be positioned against the layer of material to be measured.

This housing may take the form of a portable element, which a user brings manually towards a tyre whose thickness is to be measured. In another example, the housing may take the form of a retarder installed on a roadway, over which retarder a vehicle, fitted with a tyre whose wear is to be measured, is made to pass. In another embodiment, the housing may be integrated into the roadway so as not to retard the vehicles whose tyre wear is to be measured.

In the example of FIG. 1a, the coil 200 must be supplied with an alternating electrical signal in order to measure the thickness of the layer of rubber-like material. For this purpose, the excitation frequency of said coil should be set to an appropriate value.

This coil 200 may be modelled by the combination of a pure inductance Ls and a pure resistance with a value of Rs. This pure resistance Rs is equivalent, for a certain frequency range of the supply signal, to the sum of the ohmic resistance of the inductance and a resistive component proportional to the losses generated by the magnetic field emitted by the coil 200, in the material forming the aforementioned adjacent reinforcement.

Figure 1B:
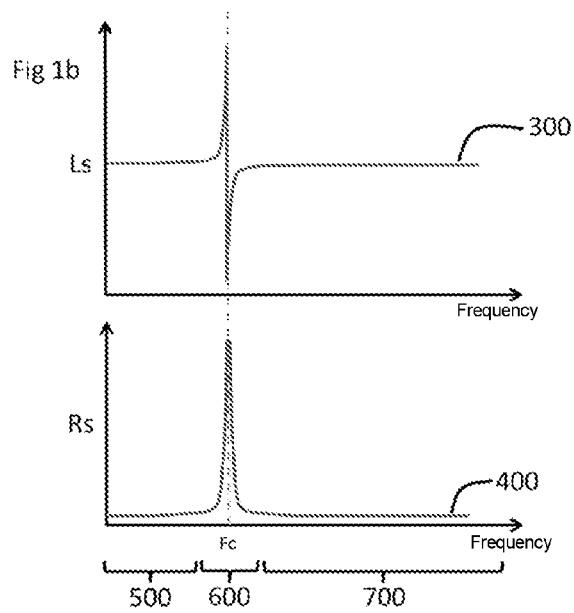

FIG. 1b shows the variation of the respective values of Ls (curve 300) and Rs (curve 400) when the supply frequency of the coil 200 is made to vary, in the absence of an adjacent reinforcement. Thus three areas of operation of the coil 200 are seen to appear.

The first area 500 corresponds to an operating mode in which the modelling of the coil 200 by an inductance placed in series with a resistance is valid.

The second area 600 corresponds to an area in which the inductance 200 acts as an anti-resonant circuit, since the value of the resistance Rs increases to such a point that said coil 200 can no longer be supplied. The positioning of the frequency Fc defining this area depends directly on the characteristics of the coil 200, which for example include, but are not limited to, the number of its turns, its ohmic resistance, the diameter of the conducting wires used to form the turns, or the nature of the material forming the turns.

The third area 700 is an area of operation in which the coil 200 is no longer simply similar to a pure inductance placed in series with a pure resistance. In this case, a capacitance Cs must be added to the model. According to the modelling schemas, this capacitance Cs may be placed in parallel with the pure inductance Ls or in parallel with the pair formed by the combination of the inductance Ls and the resistance Rs.

The area 500 is the preferred area of application of the method for measuring the thickness of a layer of rubber-like material according to the invention.

Figure 2A:
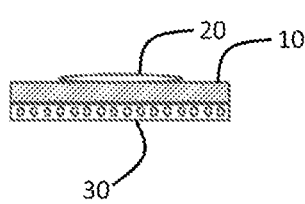
FIGS. 2a and 2b show a second example of a sensitive element used in a method according to the invention, and curves representative of the frequency response of a sensitive element of this type.

FIG. 2a shows the execution of a method according to the invention for measuring the thickness of a layer of material 10, having an adjacent reinforcement 30 on the face opposite the free face. This reinforcement 30 has been formed from steel cords assembled parallel to one another by means of a matrix of very highly resistive rubber-like material. The reinforcement formed in this way has a very low electrical conductivity, since the cords are not in contact with one another, and are connected mechanically by means of a resistive matrix. However, this reinforcement is a good magnetic field conductor, because the cables are ferromagnetic.

The first step of a method according to the invention is to position a flat coil 20 against the free face of the layer of material 10. This coil is then supplied with a supply signal whose frequency is below the cut-off frequency Fc of the coil. The variation of the resistance seen at the terminals of the coil is then measured.

As mentioned above, the coil 20 is equivalent to the combination of a pure inductance Ls and a resistance Rs. When the frequency of the supply signal of the coil 20 is made to vary, for a given distance between the coil 20 and the reinforcement 30, a variation is seen in the value of Rs.

This variation is the combination of the variation found in the absence of a reinforcement at a frequency below Fc, as shown in FIG. 1b, on the one hand, and the variation due to the presence of the reinforcement 30 near the coil 20 on the other hand.

Figure 2B:
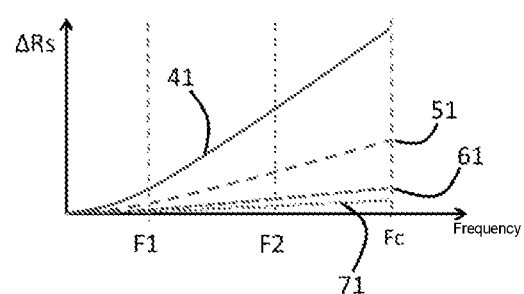
Figure 3:
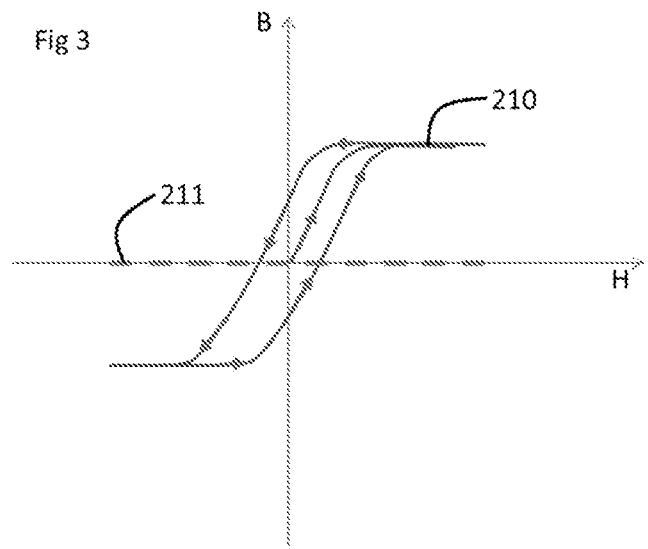
FIG. 3, described above, shows the magnetic response of a material forming an adjacent tyre reinforcement, in the context of the execution of the method according to the invention.

FIG. 2b shows the variation of the quantity ΔRs, which corresponds to the portion of the variation of Rs which is solely due to the presence of the reinforcement 30 near the coil 20. In FIG. 2b, this variation is shown as a function of the frequency of the supply signal of the coil 20.

Thus the curve 41 shows the variation of ΔRs found when the thickness of the rubber-like material 10 is one millimeter.

The curve 51 shows the variation of ΔRs found when the thickness of the rubber-like material 10 is five millimeters.

The curve 61 shows the variation of ΔRs found when the thickness of the rubber-like material 10 is ten millimeters.

Finally, the curve 71 shows the variation of ΔRs found when the thickness of the rubber-like material 10 is twenty millimeters.

In all cases, the frequency of the supply signal used remains below the frequency Fc defined in the example of FIGS. 1a and 1b.

It has been found that, if the supply frequency is set at a level F1 a long way below the frequency Fc, it is difficult to separate the variations of ΔRs obtained at this frequency F1 for a variation of layer thickness varying between one and twenty millimeters.

However, if the frequency of the supply signal is set at a higher level F2, it may be found that the variation of ΔRs can provide much better sensitivity when the thickness of the layer of rubber-like material varies between one and twenty millimeters.

In this case, it becomes possible to use the variation of ΔRs for measuring the thickness of rubber-like material.

In a variant of the method according to the invention, for high values of supply frequency of the coil 20, it is also possible to use the variation of ΔLs and ΔRs simultaneously in order to measure the layer thickness.

This is because, in this case, in the absence of eddy currents, ΔLs increases when the distance between the coil 20 and the reinforcement 30 decreases. This variation therefore follows the same direction as the variation of ΔRs, because ΔRs increases with a decrease in the distance between the coil 20 and the reinforcement 30.

Advantageously, the variation of ΔRs may be used on its own, or combined with the variation of ΔLs. This embodiment is notably, but not exclusively, used when the supply frequency of the coil 20 exceeds ten percent of the frequency Fc defined above.

Alternatively, the variation of Ls and Rs may be used directly, separately or in combination, to provide a measurement of the thickness of the layer of rubber-like material. The distance measured in this way corresponds to the distance between a free face of a layer of rubber-like material and a metallic reinforcement present in the layer. Thus, by bringing a sensitive element towards the top of a tread pattern, the tyre wear may be determined by comparing an initial distance between the top of the tread pattern and the metallic reinforcement with a measured distance.

The invention claimed is:

1. A method for measuring a thickness of a layer of rubber-like material that includes a free face in contact with air and a face joined to an adjacent reinforcement made of elements electrically insulated from one another, each of the elements containing at least one hysteretic material having a magnetic permeability greater than a magnetic permeability of air, the method comprising steps of:

causing a sensitive element, which emits an alternating magnetic field, to be moved towards the layer of rubber-like material;

measuring hysteretic losses in the adjacent reinforcement, the hysteretic losses being measured at terminals of the sensitive element; and evaluating a thickness of the layer of rubber-like material based on the hysteretic losses.

2. The method according to claim 1, wherein the step of causing the sensitive element to be moved towards the layer of rubber-like material includes applying to the free face of the layer of rubber-like material a housing in which the sensitive element is installed.

3. The method according to claim 2, wherein the housing includes, in addition to the sensitive element, an electronic measuring device.

4. The method according to claim 1, wherein the sensitive element is a solenoid formed as one of: a printed circuit, a copper wire wound with a ferromagnetic support, and a copper wire wound without a ferromagnetic support.

5. The method according to claim 1, further comprising steps of:

supplying the sensitive element with an alternating electrical signal; and causing a frequency of the alternating electrical signal to vary.

6. The method according to claim 5, wherein the frequency of the alternating electrical signal is below a cut-off frequency of the sensitive element.

7. The method according to claim 5, further comprising a step of determining an appropriate excitation frequency of the sensitive element.

8. The method according to claim 1, wherein the sensitive element is formed from turns of a coil, and wherein the step of causing the sensitive element to be moved towards the layer of rubber-like material includes positioning the sensitive element in such a way that a plane parallel to the turns of the coil is parallel to a surface of the free face of the layer of rubber-like material.

9. The method according to claim 1, wherein an electrical conductivity of the adjacent reinforcement is such that a resistivity measured between two points located on two separate elements, or a resistivity measured between two points located on a same non-metallic element, is greater than one megaohm meter.

10. The method according to claim 1, wherein an electrical conductivity of the adjacent reinforcement is such that a resistivity measured between two points located on two separate elements, or a resistivity measured between two points located on a same non-metallic element, is greater than ten megaohm meter.

* * * * *